US007256295B2

United States Patent
Thakare et al.

(10) Patent No.: US 7,256,295 B2
(45) Date of Patent: Aug. 14, 2007

(54) PROCESS FOR PRODUCING 2,3-DIAMINO-6-METHOXYPYRIDINE

(75) Inventors: D. B. Thakare, Dhulia (IN); Yashbir Singh, Ghaziabad (IN); Ashutosh Agarwal, Ghaziabad (IN)

(73) Assignee: Jubilant Organosys Limited, Noida (IN)

( * ) Notice: Subject to any disclaimer, the term of this patent is extended or adjusted under 35 U.S.C. 154(b) by 97 days.

(21) Appl. No.: 11/195,737

(22) Filed: Aug. 3, 2005

(65) Prior Publication Data

US 2006/0080790 A1    Apr. 20, 2006

(30) Foreign Application Priority Data

Oct. 15, 2004    (IN)    ............ 2027/Del/2004

(51) Int. Cl.
*C07D 211/72*    (2006.01)
(52) U.S. Cl. .................................... 546/297
(58) Field of Classification Search ............. 546/297
See application file for complete search history.

(56) References Cited

FOREIGN PATENT DOCUMENTS

CN        1453278    * 11/2003

OTHER PUBLICATIONS

Casreact Abstract 142:430268.*

* cited by examiner

*Primary Examiner*—Janet L. Andres
*Assistant Examiner*—Binta Robinson
(74) *Attorney, Agent, or Firm*—Oblon, Spivak, McClelland, Maier & Neustadt, P.C.

(57) ABSTRACT

The present invention relates to a novel process for producing 2,3-diamino-6-methxoypyridine. The process comprises neutralizing 2,3-diamino-6-methoxy pyridine dihydrochloride, which, in turn, is prepared by the reduction of 2-amino-6-methoxy-3-nitropyridine. The 2-amino-6-methoxy-3-nitropyridine is further prepared by methoxylation of 2-amino-6-chloro-3-nitropyridine by sodium methoxide in methanol.

22 Claims, No Drawings

PROCESS FOR PRODUCING 2,3-DIAMINO-6-METHOXYPYRIDINE

FIELD OF THE INVENTION

The present invention relates to a process for producing substituted diaminopyridines. More particularly, this invention provides for a novel, and industrially more suitable process for producing 2,3-diamino-6-methoxypyridine employing suitable raw materials.

BACKGROUND OF THE INVENTION

Diaminopyridines and substituted diaminopyridines are well known for their use in the composition of hair dye and in the synthesis of substituted imidazole derivatives. In the dying of hair, a dye intermediate is used, which upon oxidation, develops to form the respective dye. Oxidation dyes have acquired substantial significance for hair coloration.

There are few methods known for producing diaminopyridines and substituted diaminopyridines and the use thereof in the preparation of hair dye and in the synthesis of substituted imidazole derivatives.

German patent DE 3233540 discloses oxidation hair dye compositions, which consist of 2,3-diamino-6-methoxy pyridine and aromatic amines or diamines as precursors.

U.S. Pat. No. 3,200,040 discloses a composition suitable for use in the oxidative dying of hair, which comprises 6-methoxy-2,3-diaminopyridine, as a dye intermediate.

Voker (Seifen-Ole-Fette-Wachse, 1991, 117(4), 133–136) has investigated about 100 pyridines for their suitability as hair dyeing material and it is reported that 2,3-diamino-6-methoxypyridine dihydrochloride is one of the most potential oxidative dye couplers.

U.S. Pat. No. 226,216 discloses dye compositions, comprising one oxidation base and at least one coupler chosen from 6-alkoxy-2,3-diaminopyridine derivatives.

JP Patent No. 9241259 discloses the process for the preparation of 2,3-diamino-6-methoxypyridine and use thereof in the synthesis of 2-mercaptoimidazole condensed ring compound. The process comprises of the preparation of 2,3-diamino-6-methoxypyridine by the catalytic reduction of 2-amino-6-methoxy-3-nitropyridine. The catalytic reduction is not found suitable for commercial production due to catalyst leaching and poisoning. In addition, the free base obtained is highly colored.

U.S. Pat. No. 226,216 discloses a process for the preparation of 6-alkoxy-2,3-diaminopyridine derivatives, where 6-alkoxy-3-nitro-2-halopyridine derivative is reacted with various amines in a polar solvent chosen from alcohols, acetic acid, formic acid, dioxane and dimethyl formamide at a temperature of 75°–140° C. to obtain the corresponding 2-amino-3-nitropyridine derivative. The reduction of 2-amino-3-nitro-6-alkoxypyridine derivative is performed by hydrogenation catalyzed with palladium on carbon. This approach is not found suitable for 2,3-diamino-6-methoxypyridine.

In Aust. J. Chem., 1982, 35, 2025–34, Deady et al. has reported the route for the preparation of 2-amino-3-nitro-6-methoxypyridine, the precursor of 2,3-diamino-6-methoxypyridine. In this method, 2-amino-6-methoxypyridine was nitrated with potassium nitrate and sulfuric acid. The use of potassium nitrate is not advisable at commercial scale due to its high cost and hazardous nature. In addition, the starting material 2-amino-6-methoxypyridine is also very expensive.

EP 735025 discloses the synthesis of 6-methoxy-2-amino-3-nitropyridine by amination of 6-methoxy-3-nitropyridine by using methoxyamine, potassium-tert-butoxide and zinc chloride. The raw materials used in this process are very costly and difficult to handle.

In view of the increasing demand for 2,3-diamino-6-methoxypyridine and the lack of a robust economically viable commercial process to make that compound, there is a need to develop a commercially and economically sound process.

SUMMARY OF THE INVENTION

An object of the present invention is to provide a novel, commercially viable process for producing 2,3-diamino-6-methoxypyridine employing cost efficient and non-hazardous raw materials.

In accordance with one preferred embodiment, the present invention provides a process for producing 2,3-diamino-6-methoxypyridine, comprising neutralizing 2,3-diamino-6-methoxypyridine dihydrochloride with a base in the presence of a polar solvent.

In accordance with another preferred embodiment of the present invention, the 2,3-diamino-6-methoxypyridine dihydrochloride is prepared by the metallic reduction of 2-amino-6-methoxy-3-nitropyridine with a reducing agent in an aqueous acidic medium.

In accordance with yet another preferred embodiment of the present invention, the 2-amino-6-methoxy-3-nitro pyridine is prepared by methoxylation of 2-amino-6-chloro-3-nitropyridine using sodium methoxide in polar solvent.

In accordance with another preferred embodiment of the invention, the 2-amino-3-nitro-6-chloropyridine is producing by subjecting 2,6-dichloro-3-nitropyridine to ammonolysis.

In accordance with yet another preferred embodiment of the present invention, the 2-amino-6-chloro-3-nitropyridine is produced by nitrating 2,6-dichloropyridine with a nitrating agent.

DETAILED DESCRIPTION OF THE INVENTION

According to the preferred embodiments of the invention, there is provided a process for producing 2,3-diamino-6-methoxypyridine using cost efficient raw materials and avoiding the drawbacks related to the processes described above.

The present invention relates to a novel process for preparing 2,3-diamino-6-methoxypyridine (V) by the neutralization of 2,3-diamino-6-methoxypyridine dihydrochloride (IV) with a base in a polar solvent as described in Scheme I. The dihydrochloride derivative may be prepared by the metallic reduction of 2-amino-6-methoxy-3-nitropyridine (III). The compound (III), in turn, is prepared by the methoxylation of 2-amino-6-chloro-3-nitropyridine (II).

Scheme I

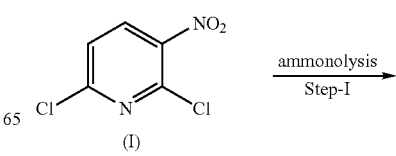

(I)

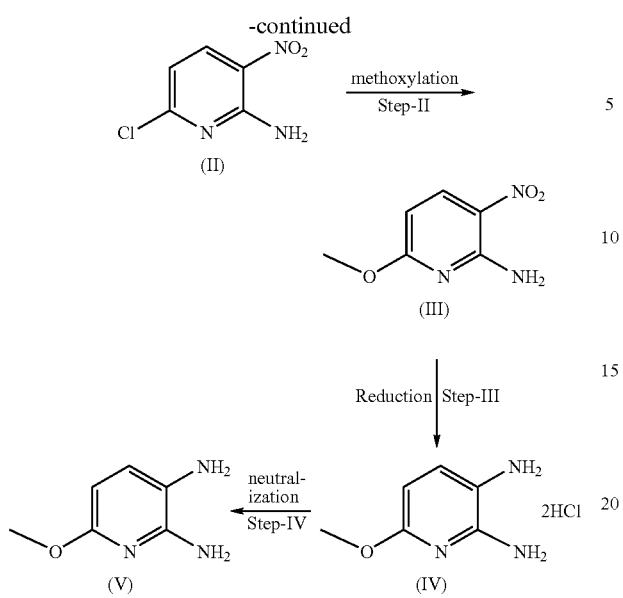

In one embodiment, the 2,3-diamino-6-methoxypyridine dihydrochloride is suspended in a polar solvent, preferably water and alcohol, more preferably in water. The pH is adjusted to 7–8 and more preferably 7.5 at a temperature between 10°–30° C., preferably at 15° C. by using inorganic or organic base. The inorganic or organic bases are preferably alkali hydroxide, alkaline hydroxide, dimethylamine, triethylamine, ammonia, aqueous ammonia more preferably aqueous ammonia. The 2,3-diamino-6-methoxypyridine thus precipitated may be isolated by filtration or extraction, preferably by filtration.

The 2,3-diamino-6-methoxypyridine dihydrochloride may be obtained by metal reduction of 2-amino-3-nitro-6-methoxypyridine. The reduction is carried out by dissolving a metal reducing agent in a polar proton donating solvent, preferably water, an alcohol or an acid. The reducing agent used is preferably iron, tin, zinc, tin chloride, zinc chloride and tin chloride dihydrate in the presence of concentrated hydrochloric acid at a temperature between 25°–80° C. More preferably the reduction is carried out in concentrated hydrochloric acid by using stannous chloride dihydrate at 35°–40° C. After the reaction is over, the mixture is cooled and 2,3-diamino-6-methoxypyridine dihydrochloride is collected by filtration or extraction preferably by filtration.

In one embodiment, the 2-amino-3-nitro-6-methoxypyridine is obtained by methoxylation of 2-amino-3-nitro-6-chloropyridine by sodium methoxide in presence of methanol at a temperature between 10°–60° C., more preferably at 25°–30° C. The molar ratio of sodium methoxide is between 1.0 and 1.5 moles, more preferably 1.05 moles. After completion of the reaction, the reaction mass is quenched in water at a temperature range between 10°–40° C., more preferably at 25°–30° C. The product is obtained by extraction or filtration, more preferably by filtration at ambient temperature.

The 2-amino-3-nitro-6-chloropyridine may be obtained by the ammonolysis of 2,6-dichloro-3-nitropyridine by a known process. The ammonolysis is carried out by using solution of aqueous ammonia in methanol at 35°–40° C. After the reaction is over, the product is obtained by filtration.

The 2,6-dichloro-3-nitropyridine may be synthesized by the nitration of 2,6-dichloropyridine with a mixture of concentrated sulfuric acid and nitric acid by the process reported in the literature. After the reaction is over, the product obtained is cooled and poured in ice water. The precipitated 2,6-dichloro-3-nitropyridine is collected by filtration.

Having generally described this invention, a further understanding can be obtained by reference to certain specific examples which are provided herein for purposes of illustration only and are not intended to be limiting unless otherwise specified.

EXAMPLES

The following examples are intended to illustrate the invention and are not to be construed as limiting the invention thereto.

Example 1

Synthesis of 2,6-dichloro-3-nitropyridine 2,6-Dichloropyridine, 25.0 gm (0.168 mole) was added slowly under constant stirring to concentrated sulfuric acid at 20°–25° C. To this solution, 75.0 gm of concentrated nitric acid (98.0%) was added slowly, keeping the reaction temperature below 50° C. After the addition, the resulting mixture was heated to 100°–105° C. for 5.0 hrs. The progress of the reaction was monitored by TLC. After the reaction was over, the reaction mixture was cooled to 50° C. and poured in ice water. The resulting precipitate was filtered and washed with water. The wet cake thus obtained was dried to give 24.5 gm of 2,6-dichloro-3-nitropyridine. The yield of 2,6-dichloro-3-nitropyridine was 75.38% and the GC purity was 99.5%.

Example 2

Synthesis of 2-amino-6-chloro-3-nitropyridine 2,6-Dichloro-3-nitropyridine, 25.0 gm (0.129 mole) was dissolved in methanol (50.0 ml) at room temperature. To the solution thus obtained, 25.0% aqueous ammonia solution 12.2 ml (0.179 mole) was charged at room temperature. The resulting mixture was heated to 35°–40° C. for 2.0 hrs. The reaction was monitored by TLC. After the completion of the reaction, the mixture was cooled to 20° C. The solid obtained was washed, filtered with methanol and dried to yield 12.50 gm of 2-amino-6-methoxy-3-nitro pyridine (56.45%) with the HPLC purity of 99.3%: Melting point 192°–195° C.; 1HNMR: (DMSO D6) δ6.75–6.77 ppm (d, 1H), δ8.38–8.40 (d, 1H).

Example 3

Synthesis of 2-amino-6-methoxy-3-nitropyridine

Sodium methoxide, 7.78 gm (0.144 mole) and methanol 50.0 ml were mixed and cooled to 15° C. To this solution, 25.0 gm of 2-amino-6-chloro-3-nitropyridine (0.144 mole) was added while maintaining the temperature at 15° C. by external cooling. The resulting mixture was heated to 25°–30° C. and maintained at this temperature for 4–5 hrs with constant stirring. The completion of reaction was monitored by TLC. After the completion of reaction, the reaction mixture was poured in water. The precipitate thus obtained was filtered and washed with water. On drying 21.0 gm of 2-amino-3-nitro-6-methoxypyridine (86.5% yield) was obtained, with the HPLC purity of 99.0%. Melting point 167°–169° C.; $^1$HNMR (CDCl$_3$) δ3.89 ppm (s, -3H, OCH3), 66.14–6.16 ppm (d, 1H), 68.24–8.27 ppm (d, 1H), 68.16 ppm (s, -2H, —NH$_2$)

Example 4

Synthesis of 2,3-diamino-6-methoxypyridine dihydrochloride

To the concentrated hydrochloric acid (250 ml), 25.0 gm of 2-amino-6-methoxy-3-nitropyridine (0.147 mole) was added at room temperature. The resulting solution was cooled to 15° C. and 66.7 gm of stannous chloride dihydrate (0.294 mole) was added slowly. The reaction mass was heated to 35°–40° C. and mixed for 5–6 hrs with constant stirring. The reaction was monitored by TLC. After the reaction was over, the reaction mixture was cooled to 20° C. and stirred for one hour. The resulting mixture was filtered and dried to give 27.0 gm of 2,3-diamino-6-methoxypyridine dihydrochloride (yield=86.4%); Melting point 211 to 213° C.; HPLC purity was 99.0%.

Example 5

Synthesis of 2,3-diamino-6-methoxypyridine 2,3-Diamino-6-methoxypyridine dihydrochloride, 25.0 gm (0.117 mole) was suspended in water (50.0 ml) and the mixture was cooled to 15° C. After cooling, the reaction mixture was neutralized with 25% aqueous ammonia solution to the pH of 7.0 to 8.0. The separated precipitate was stirred for half an hour and then filtered out. After drying under vacuum 14.95 gm of 2,3-diamino-6-methoxypyridine (92.0% yield) was obtained with a purity of 99.01% by HPLC.

$^1$HNMR (DMSO D6) δ3.67 ppm (s, 3H, —OCH$_3$), δ7.47–7.49 (d, 1H), δ6.01–δ6.11 (d, 1H).

Certain modifications and improvements of the disclosed invention will occur to those skilled in the art without departing from the scope of invention, which is limited only by the appended claims.

This application is based on Indian patent application serial No. 2027/DEL/2004, filed on Oct. 15, 2004, and incorporated herein by reference.

We claim:

1. A process for producing 2,3-diamino-6-methoxypyridine comprising neutralizing 2,3-diamino-6-methoxypyridine dihydrochloride with a base in the presence of a polar solvent.

2. The process according to claim 1, wherein the base is selected from triethylamine or aqueous ammonia.

3. The process according to claim 2, wherein the base is an aqueous solution of ammonia.

4. The process according to claim 1, wherein the base is an inorganic or organic base.

5. The process according to claim 1, wherein the base is alkali hydroxide, alkaline hydroxide, dimethylamine, triethylamine or ammonia.

6. The process according to claim 1, wherein the polar solvent is selected from the group consisting of water, alcohol, and mixtures thereof.

7. The process according to claim 4, wherein the polar solvent is water.

8. The process according to claim 4, wherein the polar solvent comprises water.

9. The process according to claim 1, further comprising reducing 2-amino-6-methoxy-3-nitropyridine with a reducing agent in presence of an aqueous acidic medium to produce the 2,3-diamino-6-methoxypyridine dihydrochloride.

10. The process according to claim 9, wherein the reducing agent is a metal reducing agent dissolved in a polar proton donating solvent.

11. The process according to claim 9, wherein the metal reducing agent is stannous chloride dihydrate.

12. The process according to claim 9, wherein the reaction is carried out at a temperature of 25–80° C.

13. The process according to claim 12, wherein the reaction is carried out at a temperature of 30–40° C.

14. The process according to claim 9, wherein the polar proton donating solvent is concentrated hydrochloric acid.

15. The process according to claim 9, further comprising methoxylating 2-amino-6-chloro-3-nitropyridine with sodium methoxide in presence of a polar solvent to produce the 2-amino-6-methoxy-3-nitropyridine.

16. The process according to claim 15, wherein the polar solvent is methanol.

17. The process according to claim 15, wherein the reaction is carried out at a temperature of 10–60° C.

18. The process according to claim 15, wherein the reaction is carried out preferably at a temperature of 25–30° C.

19. The process according to claim 15, further comprising ammonolyzing 2,6-dichloro-3-nitro pyridine to produce the 2-amino-3-nitro-6-chloropyridine.

20. The process according to claim 19, wherein the ammonolysis is carried out using a solution of aqueous ammonia in methanol.

21. The process according to claim 19, further comprising nitrating 2,6-dichloropyridine with a nitrating agent to produce the 2,6-dichloro-3-nitropyridine.

22. The process according to claim 21, wherein the nitrating agent is mixture of concentrated sulfuric acid and nitric acid.

* * * * *